US00PP22207P3

(12) United States Plant Patent
Brown et al.

(10) Patent No.: US PP22,207 P3
(45) Date of Patent: Oct. 25, 2011

(54) APPLE TREE NAMED 'NEW YORK'

(50) Latin Name: *Malus domestica*
Varietal Denomination: New York 2

(75) Inventors: Susan K. Brown, Geneva, NY (US); Kevin Maloney, Phelps, NY (US)

(73) Assignee: Cornell University, Ithaca, NY (US)

( * ) Notice: Subject to any disclaimer, the term of this patent is extended or adjusted under 35 U.S.C. 154(b) by 29 days.

(21) Appl. No.: 12/653,612

(22) Filed: Dec. 15, 2009

(65) Prior Publication Data

US 2011/0145957 P1 Jun. 16, 2011

(51) Int. Cl.
*A01H 5/00* (2006.01)

(52) U.S. Cl. ..... Plt./161

(58) Field of Classification Search ..... Plt./161, Plt./172

See application file for complete search history.

*Primary Examiner* — Kent L Bell

(74) *Attorney, Agent, or Firm* — Harris Beach PLLC

(57) ABSTRACT

A new and distinct *Malus domestica* apple tree cultivar named 'New York 2' that is characterized by having red, juicy, crisp fruits with a firm texture and tart flavor that ripen mid to late season. The fruit of 'New York 2' has a very long storage life (100-150 days) while maintaining fresh quality. Trees are annually productive, grower friendly and fruits are not subject to pre-harvest drop and have good retention on the tree. 'New York 2' was tested as NY 92609-463.

5 Drawing Sheets

Latin name of the genus and species of the plant claimed: *Malus domestica.*

Variety denomination: 'New York2'.

BACKGROUND OF THE INVENTION

The present invention relates to a new and distinct variety of apple tree botanically known as *Malus domestica* 'New York 2' and hereinafter referred to by the variety denomination of 'New York 2'.

'New York 2' was selected for its precocious tree habit and excellent fruit characteristics at harvest and after a period in cold storage. 'New York 2' fruit are very firm, crisp, juicy, and tart.

The new variety was derived from crossing the apple variety 'Braeburn' with the apple variety 'Autumn Crisp' in 1992. 'Braeburn' is a hybrid of 'Lady Hamilton' by an unknown pollen parent. 'Autumn Crisp' is a hybrid of 'Golden Delicious'×'Monroe' and 'Monroe' is a hybrid of 'Jonathan'× 'Rome Beauty'. One seedling, designated NY 92609-463, was selected from a population of 1,017 seedlings from this cross. Pollination, cultivation and selection were conducted in Geneva, N.Y.

NY 92609-463 is being named and released as 'New York 2' and is the subject of this invention.

Asexual reproduction by budding of the new cultivar 'New York 2' in Geneva, N.Y. by the inventors shows that the unique combination of characteristics of asexually propagated trees are true to form and transmitted through succeeding propagations.

BRIEF SUMMARY OF THE INVENTION

The following traits of the new cultivar 'New York 2' have been observed and documented in multiple years. The observations and description were collected from test trees grown in Geneva, N.Y. and other test sites within New York State.

The new variety is distinguishable from the parent varieties 'Braeburn' and 'Autumn Crisp.' Multiple features distinguish the new variety from the parent varieties.

'Braeburn' fruit have orange-red fruit color, slightly oblique fruit shape, and later maturity when compared to 'New York 2.' 'Autumn Crisp' fruit has earlier maturity, red blush color on a yellow/green background, and a globose fruit shape when compared to 'New York 2.' 'New York 2' has large fruit size and a brighter and deeper and more uniform red color pattern of fruit. Fruit of 'New York 2' mature after 'Autumn Crisp' and before 'Braeburn.'

'New York 2' has foliage similar to 'Braeburn,' is annually productive and the fruits are retained without pre-harvest drop similar to its 'Autumn Crisp' parent.

'New York 2' has not been grown and observed in all geographic locations and all possible climatic conditions. Slight phenotypic variations might be observed over locations without any change to the genotype.

BRIEF DESCRIPTION OF THE DRAWINGS

The accompanying color photographs illustrate typical specimens of the foliage and fruit and typical anatomical characteristics of the new *Malus* variety 'New York 2,' showing the colors as true as is reasonably possible with colored reproductions of this type. Colors in the photographs may differ slightly from the color values cited in the detailed botanical description, which accurately describe the color of 'New York 2.'

View A is a cross-sectional view of 'New York 2' fruit cut longitudinally.
View B is a side view.
View C is a top (stem-end) view.
View D is a bottom (calyx end) view.
View E is a side view.
View F is a cross-sectional view of 'New York 2' fruit cut horizontally.

Figure 1:
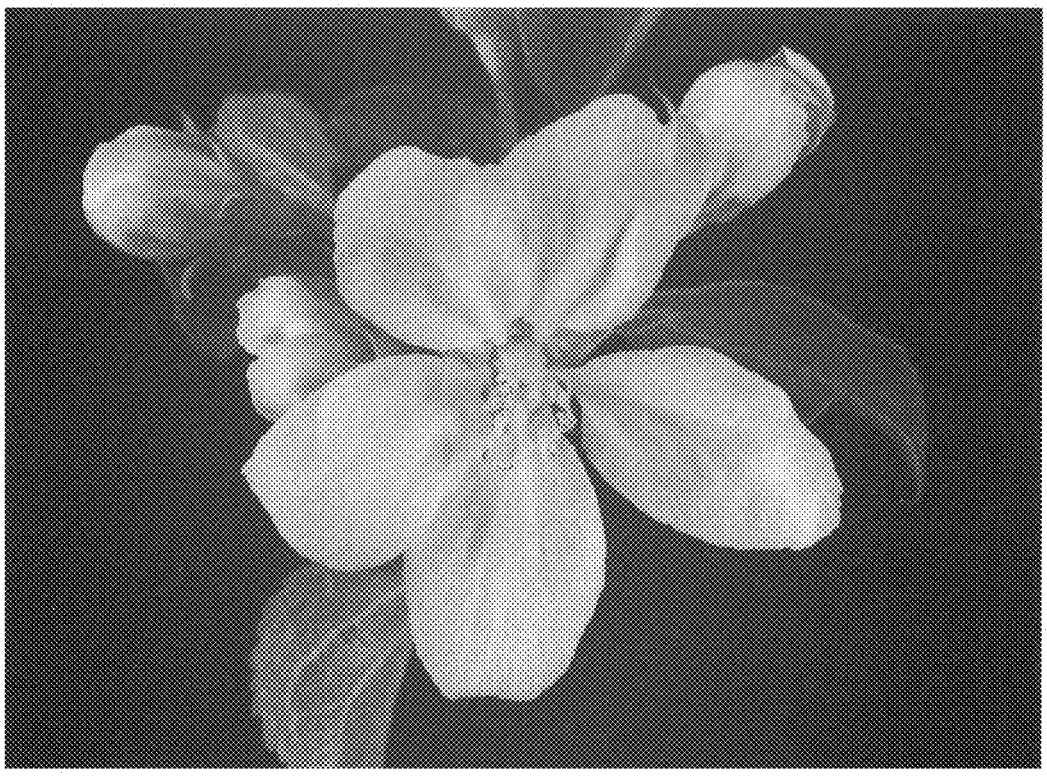
FIG. 1 shows a 'New York 2' flower cluster with the primary (dominant) flower open.
Figure 2:
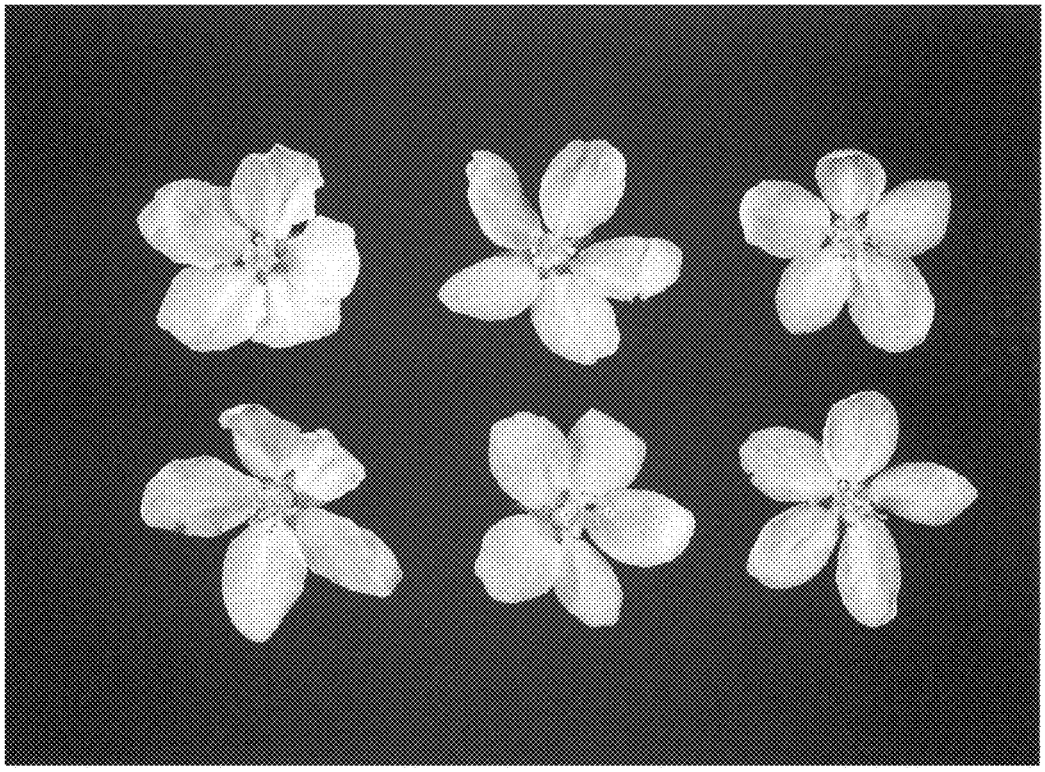
FIG. 2 shows 6 different flowers, two flowers each (from left to right) of the variety 'Braeburn' (far left), 'New York 2' (middle) and 'Autumn Crisp' (far right).
Figure 3:
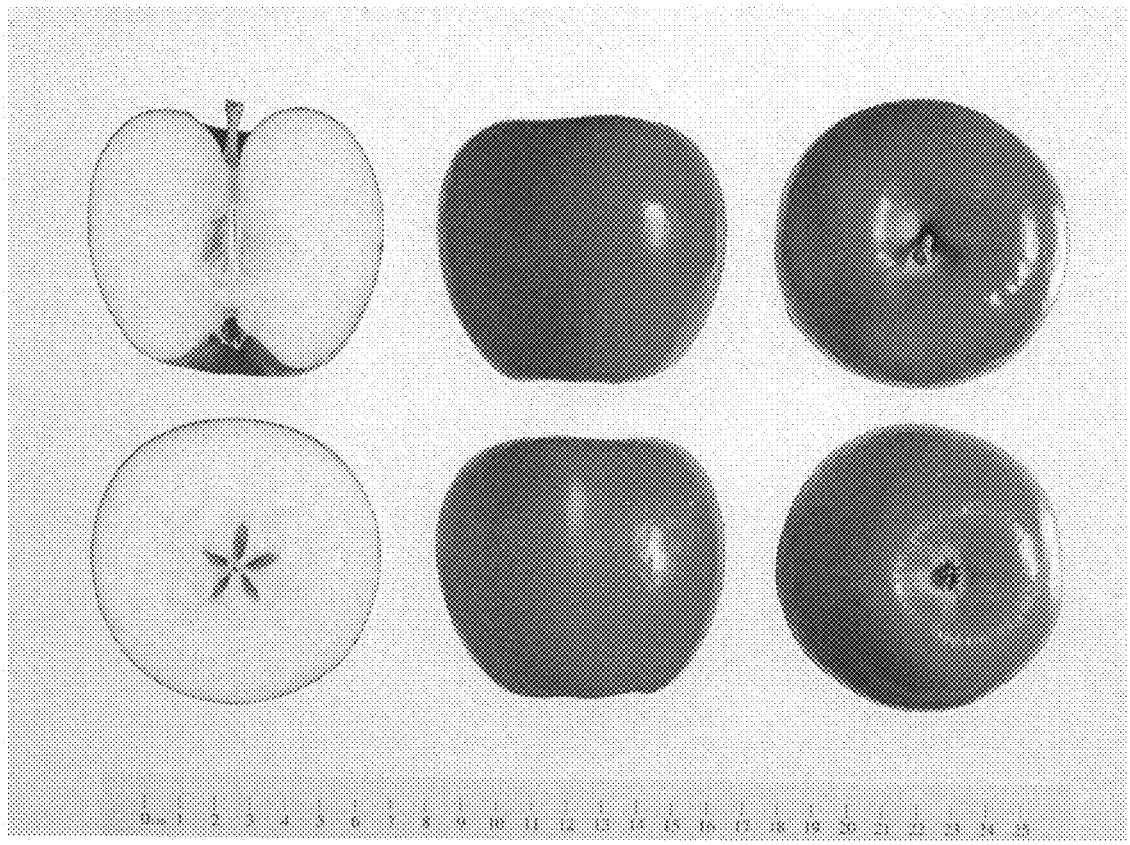
FIG. 3 shows six views of representative apples of 'New York 2.' Beginning in the upper left corner and proceeding clockwise.
Figure 4:
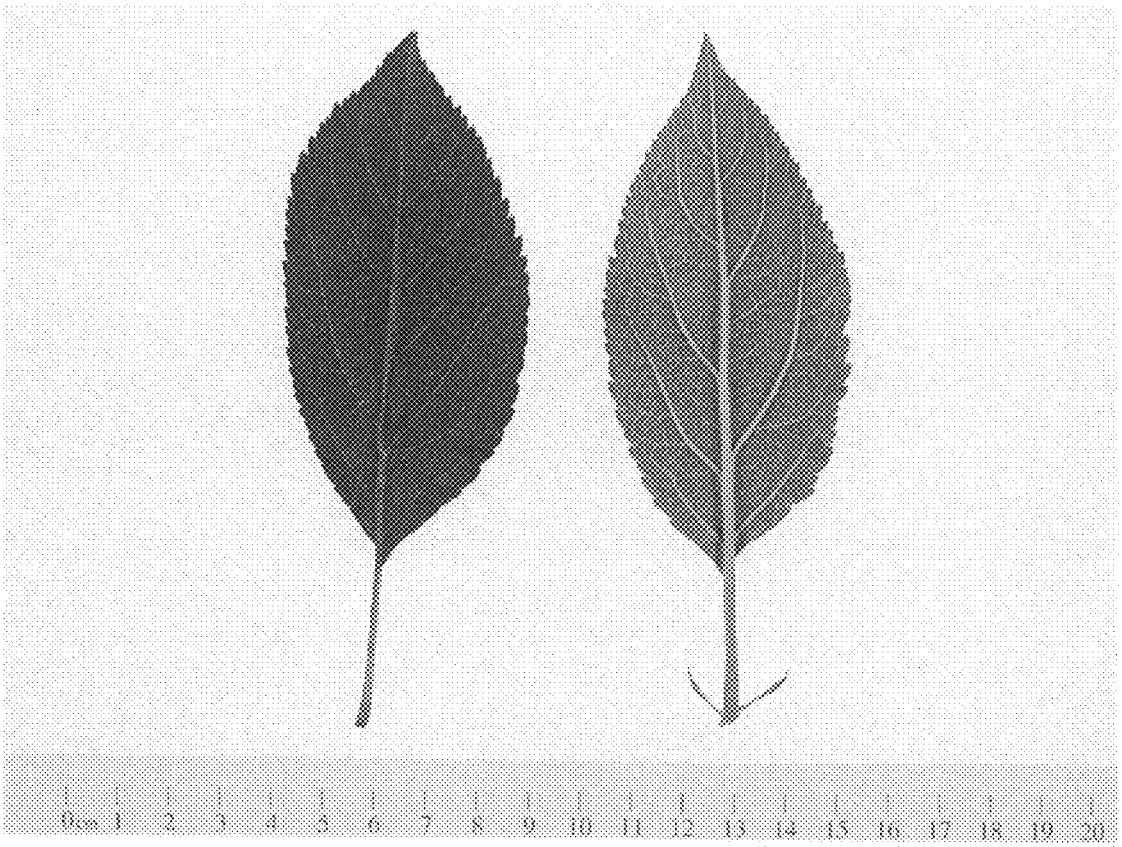

FIG. 4 shows two mature leaves of 'New York 2,' one top view and one bottom view.

Figure 5:
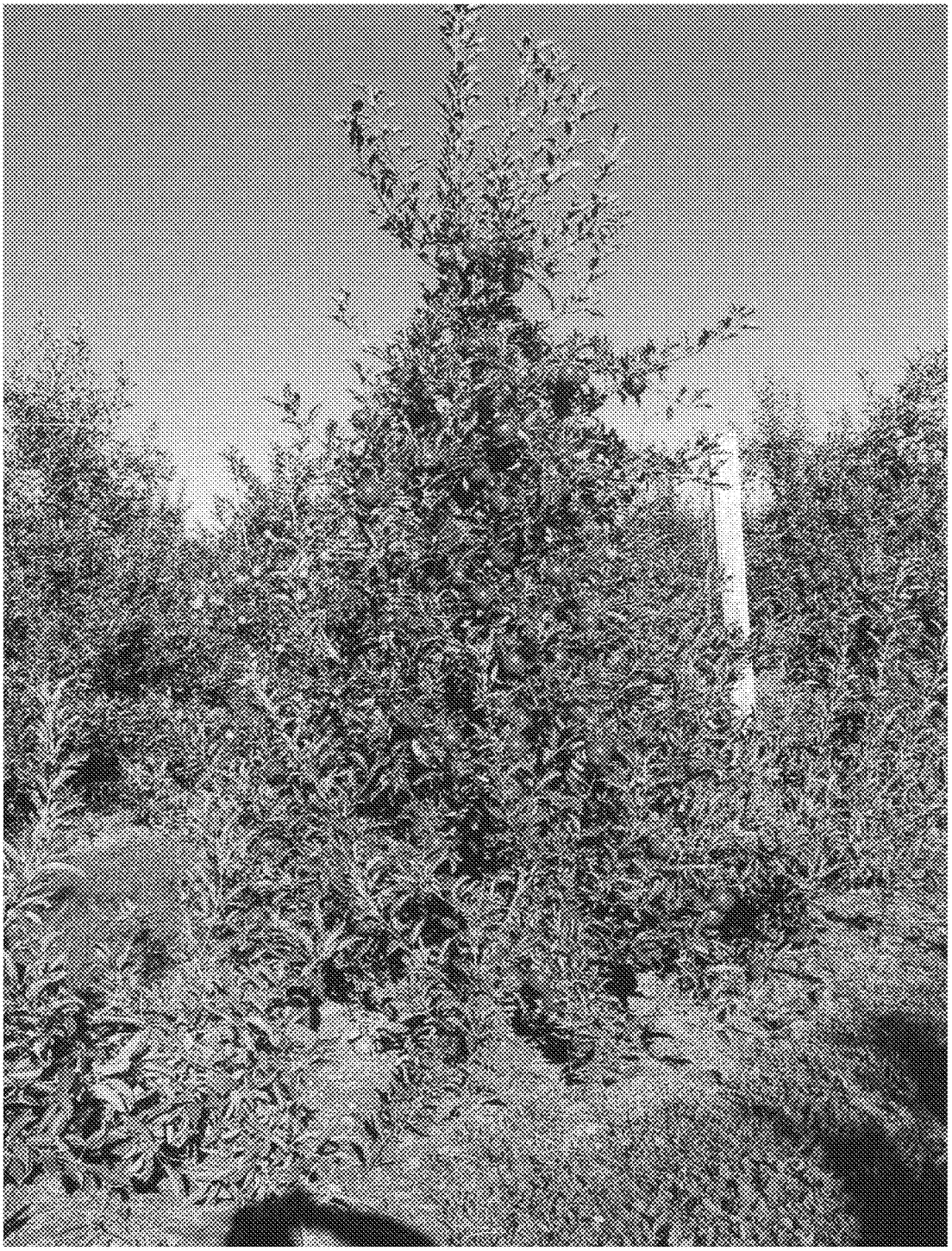

FIG. 5 is a young tree of 'New York 2.'

Figure 6:
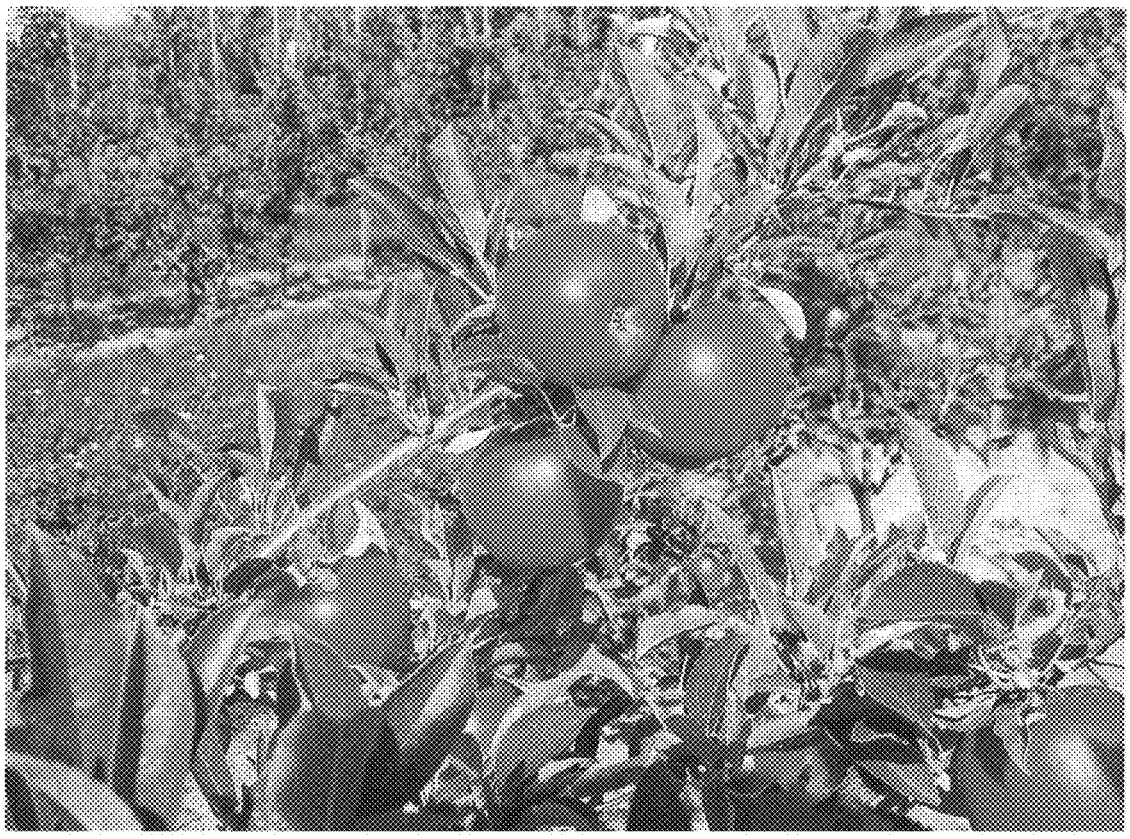

FIG. 6 shows 'New York 2' apples on the tree.

DETAILED BOTANICAL DESCRIPTION

The following is a detailed botanical description of the new variety with color terminology in accordance with The Royal Horticultural Society Colour Chart (R.H.S.C.C.) except where general color terms of ordinary meaning are used as is clear from the context.

The specimens described were grown at Geneva, N.Y. in the United States of America. The observations were made on trees grown from 1993 to 2009.

Flowering begins on average by May 9th and full bloom is by May 13th in Geneva, N.Y. The fruit ripen for eating towards mid to late season. Specifically harvest commences on about October 13th and ends about October 28$^{th}$ in Geneva, N.Y.

Trees: Medium; spreading habit; early bearing on spurs; vigor medium. Four-year-old trees have an average height of 2.5 m and spread of 1.3 m.

Trunk: Smooth, medium size, four-year-old trees have an average trunk diameter of 3.3 cm measured at 30 cm above the graft union; bark is RHSCC Greyed-Orange 177B. Trunk lenticels average 8 to 10 per square centimeter, lenticels RHSCC Grey-Brown 199D, length 1.5 mm to 10 mm and width 1.5 mm to 3.0 mm.

Branches: Moderately thick; smooth; multi-branching; the angle of branching being commonly 30-40 degrees above the horizontal. Four-year-old trees have an average of 16 branches per tree, 77 cm in length, 1.6 cm in diameter. Average internode length on a one-year-old shoot is 2.8 cm. Branch color RHSCC Brown 200D. Branch lenticels medium to high density average 10 to 12 per square centimeter, RHSCC Grey-Brown Group 199C, length 1 mm to 4 mm and width 0.7 mm to 1.5 mm. Branches on four-year-old trees have on average 12 spurs per branch, average spur length 5.2 cm, average spur diameter 5.7 mm, RHSCC Brown 200D.

Leaves: Medium size, ovate in shape with an acute apex and obtuse base, upward pose, concave-convex in cross section, serrate indentation of margin, medium glossiness of upper sides; medium pubescence on lower side; medium stipule size; stipules are free and lateral, spinrose in shape, 5 mm to 8 mm in length and 0.1 mm to 0.2 mm in width; medium time of bud burst between April 12 to April 17 on average in Geneva, N.Y. Average leaf blade length 116 mm, blade width 53 mm averages 3.8 serrations per cm of leaf blade margin. The color of the upper surface of the leaf blade is most similar to RHSCC 147A, the bottom surface of the leaf blade is most similar to RHSCC 146A, the veins are RHSCC145C. Petioles are RHSCC 148D, medium to long in length, petiole length 40 mm, petiole diameter 1.4 mm to 2.2 mm.

Flowers: Medium time of beginning of flowering (10% open flowers) on a average May 6 to May 10 in Geneva, N.Y.; six flowers per spur, un-open flower bud shape is ovoid to round, length from base of ovary to tip of flower is 16 mm to 22 mm and 9 mm and to 15 mm in diameter, bud color of unopened flower RHSCC red group 54A. Open flowers in cluster overlap, large size, 52 mm flower diameter and 20 mm height; flat shape; margins of petals slightly overlap.

Flower petal: Upper surface RHSCC White 155B, lower surface RHSCC Ref-Purple 70C, 5 petals per flower, petal shape is oval, margin smooth to slightly undulate, apex rounded, base ovate and wide, petal length 23 mm, petal width 16 mm.

Flower pedicel: RHSCC yellow green 148A, length 26 mm, width 1.5 mm.

Stamens: 22 stamens per flower, 9-12 mm long, stamen color RHSCC green white group 157C. Anther color RHSCC greyed yellow 162C.

Style: 6-10 mm long, 5 styles per flower, style color RHSCC Greyed Green 195C, stigma color RHSCC Grey Brown 199C.

Sepals: 5 per flower, upper surface color RHSCC yellow-green group 146B and tinged at tip RHSCC Greyed-Purple 184A, lower surface color RHSCC Yellow-Green 146B, sepal length 8 mm, sepal width 2 mm, apex pointed, deltoid in shape, margin smooth, slightly reflexed, nearly flat position, 22 anthers per flower.

Fruit:

*Fruit.*—Examined at maturity.
*Brix.*—13.7°.
*Acidity.*—0.61% malic acid as measured by titration.
*Lbs. Pressure.*—16 to 21 as measured by penetrometer.
*Size.*—Large to very large; axial diameter (8.2 cm), transverse diameter (7.2 cm), weight 210 grams.
*Shape.*—Uniform; globose; symmetrical in side view; medium crowning at distal end.
*Cavity.*—Obtuse. RHSCC yellow-green 152C and ranging from 152A to 152D. Depth 12.2 mm, width 28.8 mm.
*Basin.*—Wide, broad breadth; wavy. Depth 11.4 mm, width 29.2 mm, RHSCC Red 46A.
*Stem.*—Medium thickness 2.0 mm; medium length 15.6 mm, RHSCC Yellow Green 146C and tinged Greyed-Purple 184B.
*Calyx.*—Persistent, partially closed, erect.
*Calyx tube.*—Cone shaped.
*Stamen remnants.*—Median.
*Core lines.*—Meeting, length 34 mm and width 36 mm.
*Core position.*—Median, closed core, medium core (24.3 mm in width).
*Carpels.*—Ovate, inner surface of carpel slightly tufted.
*Skin.*—Medium-thick; 0.24 mm; smooth; bloom of skin, scant; cracking tendency of skin, absent; background color, RHSCC greyed-yellow 160B. Prominent lenticels, round shape, 0.3 mm to 0.9 mm diameter, 3 to 4 per square centimeter, RHSCC Orange White 159C.
*Over-color.*—Approximately eighty percent of over-color of skin; red, RHSCC greyed purple 185A mostly solid blush with small dots.
*Flesh.*—Juicy, crisp, firm, RHSCC White 155B, rich complex aroma.
*Texture.*—Crisp, slightly coarse, firm.
*Flavor.*—Tart and pleasant mild flavor.
*Weight of fruit.*—210 gm.
*Quality.*—Very good, fresh, juicy, firm and crisp.

*Seeds.*—Five locules (average length 22 mm and width 11 mm); 9 to 11 seeds total, seed length 10.4 mm, seed width 4.8 mm, seed depth 2.7 mm, acuminate and acute, tufted, dried color RHSCC 165A.

*Use.*—Market; dessert, fresh slice, multiple.

*Keeping quality.*—Excellent: no disorders after 100 days.

*Resistance to insects.*—Good.

*Resistance to diseases.*—Good, but moderately susceptible to powdery mildew (*Podosphaera leucotricha*) of the foliage.

*Production.*—Early, regular cropping and very precocious. Fruit yields of 75 to 250 fruits per mature tree have been observed.

*Growth habit.*—Standard, fruit borne on short spurs.

*Winter hardiness.*—Very winter hardy. No winter injury observed on trees grown in USDA Plant Hardiness Zones 4b, 5a, 5b and 6a over several seasons.

*Management.*—Trees require pruning in winter and fruit thinning in early summer. Trees in test plot trained as center leader or slender spindle trees. Natural habit is medium vigor, rounded crown (fruiting leader), with many branches. 'New York 2' has been successfully grown on EMLA 9 and M.9 (337) rootstocks.

What is claimed is:

1. A new and distinct *Malus domestica* apple tree variety named 'New York 2' as described and illustrated herein.

* * * * *

UNITED STATES PATENT AND TRADEMARK OFFICE

CERTIFICATE OF CORRECTION

PATENT NO. : PP22,207 P3
APPLICATION NO. : 12/653612
DATED : October 25, 2011
INVENTOR(S) : Susan K. Brown et al.

It is certified that error appears in the above-identified patent and that said Letters Patent is hereby corrected as shown below:

On the Cover Page at paragraph (54) please delete the words "NEW YORK" and replace with --'NEW YORK 2'--

Signed and Sealed this
Twelfth Day of June, 2012

David J. Kappos

David J. Kappos
*Director of the United States Patent and Trademark Office*